(12) United States Patent
Chen

(10) Patent No.: US 6,540,697 B2
(45) Date of Patent: Apr. 1, 2003

(54) SAFETY VACUUM SYRINGE FOR BLOOD SAMPLING CONFORMED TO ERGONOMICS

(76) Inventor: Long Hsiung Chen, 4F, No. 29, Lane 286, Shih Tung Rd., Shih Lin Dist., Taipei (TW)

( * ) Notice: Subject to any disclaimer, the term of this patent is extended or adjusted under 35 U.S.C. 154(b) by 0 days.

(21) Appl. No.: 10/141,066

(22) Filed: May 9, 2002

(65) Prior Publication Data

US 2002/0133091 A1 Sep. 19, 2002

Related U.S. Application Data

(62) Division of application No. 09/765,356, filed on Jan. 22, 2001.

(51) Int. Cl.[7] .................................................. A61B 5/00
(52) U.S. Cl. .................... 600/576; 600/577; 600/573; 604/181
(58) Field of Search ............................... 600/576, 573, 600/577; 604/181, 239, 240, 187

(56) References Cited

U.S. PATENT DOCUMENTS

| | | | | |
|---|---|---|---|---|
| 3,326,206 A | * | 6/1967 | Barr, Sr. et al. | |
| 4,280,509 A | * | 7/1981 | Bethkenhagen et al. | .... 600/577 |
| 4,326,541 A | * | 4/1982 | Eckels | .......... 600/577 |
| 4,549,554 A | * | 10/1985 | Markham | |
| 4,619,272 A | * | 10/1986 | Zambelli | |
| 4,747,831 A | * | 5/1988 | Kulli | |
| 4,841,985 A | * | 6/1989 | Wanamaker | ........... 600/576 |
| 4,844,089 A | * | 7/1989 | Roberti | ........... 600/577 |
| 4,972,843 A | * | 11/1990 | Broden | ........... 600/576 |
| 4,993,426 A | * | 2/1991 | Spencer | ........... 600/576 |
| 5,117,837 A | * | 6/1992 | Wanamaker et al. | ........ 600/576 |
| 5,201,716 A | * | 4/1993 | Lewis | ........... 600/576 |
| 5,259,392 A | * | 11/1993 | Schmitt | ........... 600/576 |
| 5,413,115 A | * | 5/1995 | Baldwin | ........... 600/576 |
| 5,655,541 A | * | 8/1997 | Vattuone | |
| 5,797,490 A | * | 8/1998 | Fujii et al. | ........... 600/576 |
| 6,102,894 A | * | 8/2000 | Dysarz | ........... 600/576 |
| 6,132,402 A | * | 10/2000 | Tessmann et al. | |
| 6,152,901 A | * | 11/2000 | Arruego et al. | ............ 600/576 |

FOREIGN PATENT DOCUMENTS

EP         Wo 89/05118      *  6/1989

* cited by examiner

Primary Examiner—Timothy L. Maust
Assistant Examiner—Khoa Huynh
(74) Attorney, Agent, or Firm—Rosenberg, Klein & Lee

(57) ABSTRACT

An ergonomic safety vacuum syringe for sampling blood comprises a vacuum, a hollow barrel, a first needle, a second needle, and a press plate. The hollow barrel includes an end surface and a cylindrical side surface, with a trench formed through the end surface. A needle seat is coupled to the trench, and a sliding slit is formed through the end surface and cylindrical side surface. The syringe also comprises a first needle coupled to a reduced inlet disposed on the hollow barrel and the second needle having Z-shaped portion formed between opposing first and second end portions. The first end is received within the reduced inlet, while the second end portion is positioned along a central axis of the hollow barrel. Further, the press plate is positioned within the sliding slit of the hollow barrel.

14 Claims, 15 Drawing Sheets

SAFETY VACUUM SYRINGE FOR BLOOD SAMPLING CONFORMED TO ERGONOMICS

This application is a divisional of copending application (s) application Ser. No. 09/765,356 filed on Jan. 22, 2001.

FIELD OF THE INVENTION

The present invention relates to a safety vacuum syringe for blood sampling conformed to ergonomics, and more particularly to the syringe that not only conforms to ergonomics in use but may receive the conventional needle head and the vacuum tube so as to lower production cost.

BACKGROUND OF THE INVENTION

Many viruses and diseases or body functions can be examined by a blood test, which makes the blood test to be a regular and frequent job. For preventing a patient from infecting lethal virus or germ, the selection of blood sampling tool will be very important during a blood sampling is processing. Therefore, if we want to do blood sampling more safely, blood sampling must have some degree of improvement.

The needle head of a conventional blood sampling syringe, as revealed in America granted patent U.S. Pat. No. 5,423,758, is disposed at the central axis of the front end of the syringe. When a blood sampling is processing, the needle of a syringe is struck into a patient's vein to draw out the blood in the vein. But the angle between such kind of syringe and the skin surface of a human body is larger when a blood sampling is processing for the reason that the needle head is at the center of syringe, the needle head is uneasy to be struck into vein to draw blood. Especially to the patients whose blood vessels are thinner, the blood vessel is always easy to be struck through so that blood sampling can not be done smoothly.

SUMMARY OF THE INVENTION

It is one object of the present invention to provide a safety vacuum syringe for blood sampling conformed to ergonomics, a needle head is eccentrically disposed at the front end of a syringe so as to lower the blood sampling angle when a blood sampling is processing to let blood sampling be done smoothly.

Another object of the present invention is to provide a safety vacuum syringe for blood sampling, wherein an inner needle tip of the needle head has a substantially Z-shaped portion so that it can be positioned at the center of the needle head to fit for use in the manner of a traditional vacuum blood collecting cup.

Still another object of the present invention is to provide a conventional needle head can be used according to users' need.

BRIEF DESCRIPTION OF THE DRAWING

The present invention can be better understood by detailed description of the following drawings, in which.

DETAILED DESCRIPTIONS OF THE INVENTION

Figure 1:
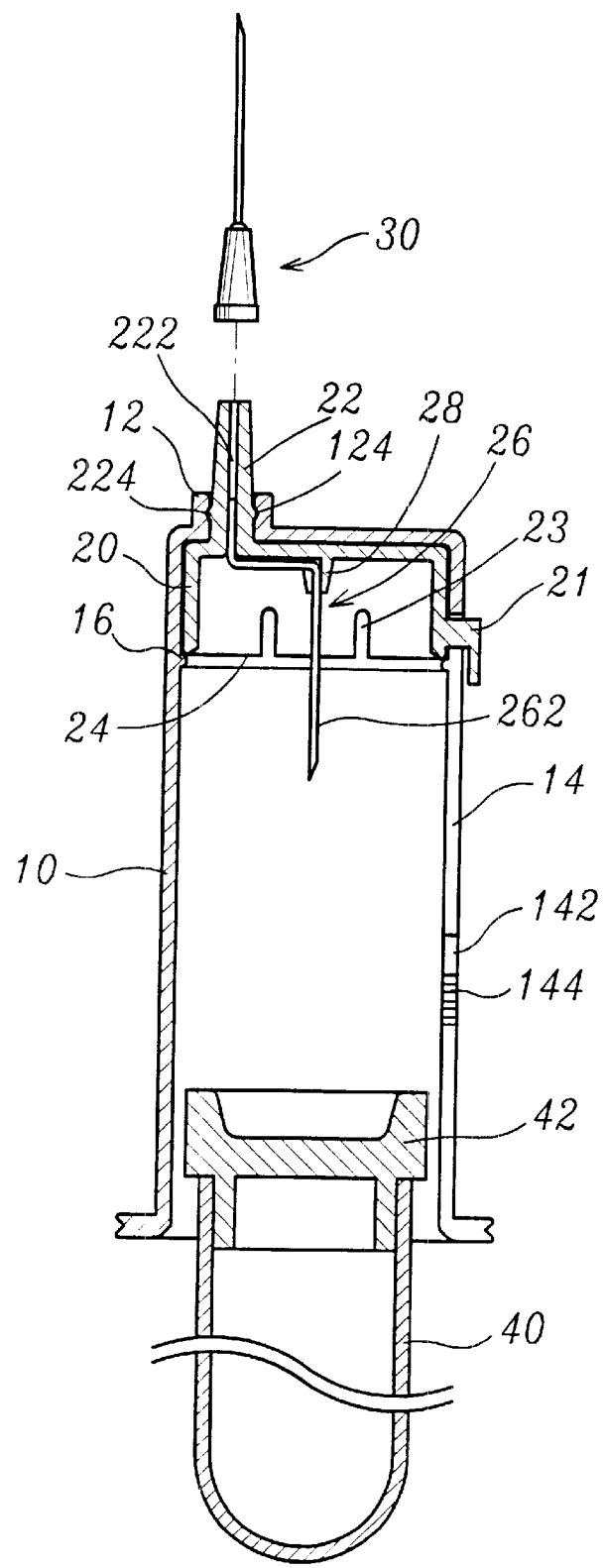
FIG. 1 is a longitudinal sectional view of a preferred embodiment of the present invention before a needle holder is hitched on a syringe.
Figure 2:
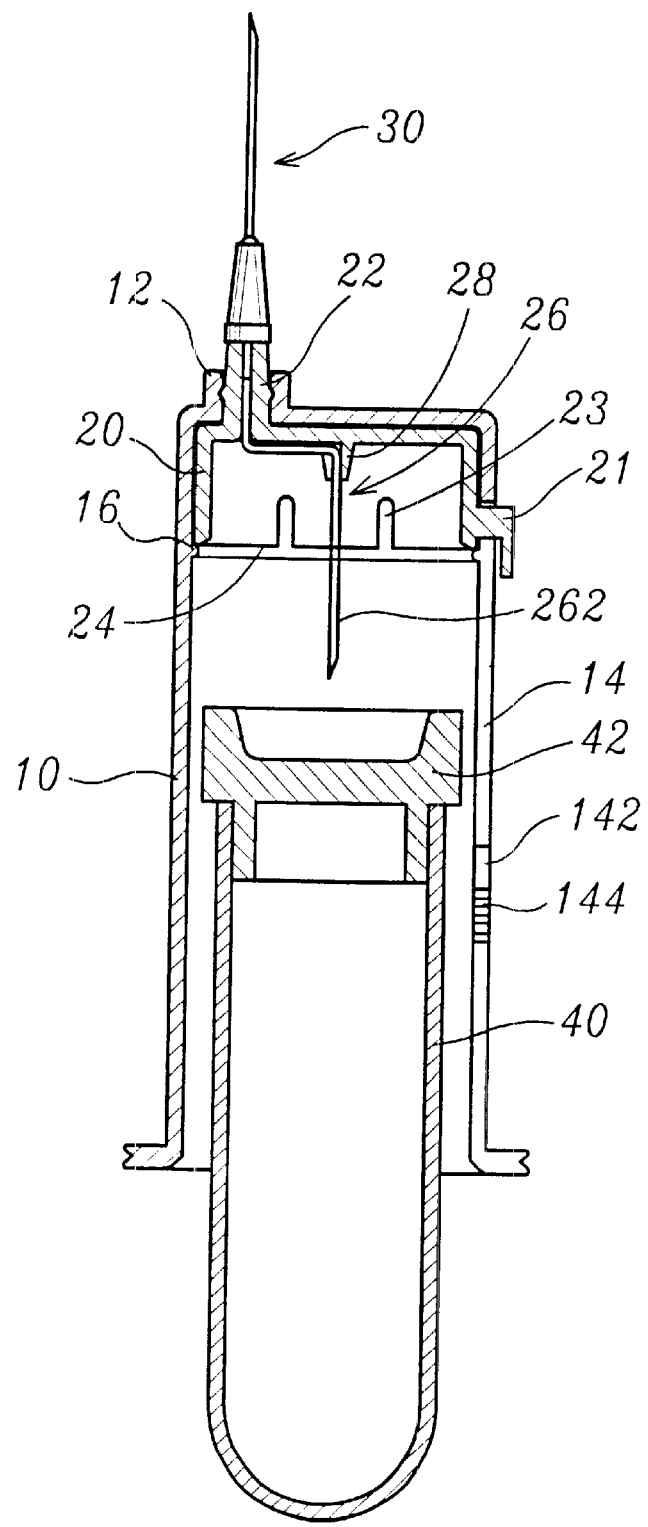
FIG. 2 is a longitudinal sectional view of a preferred embodiment of the present invention after a needle holder is hitched on a syringe.
Figure 3:
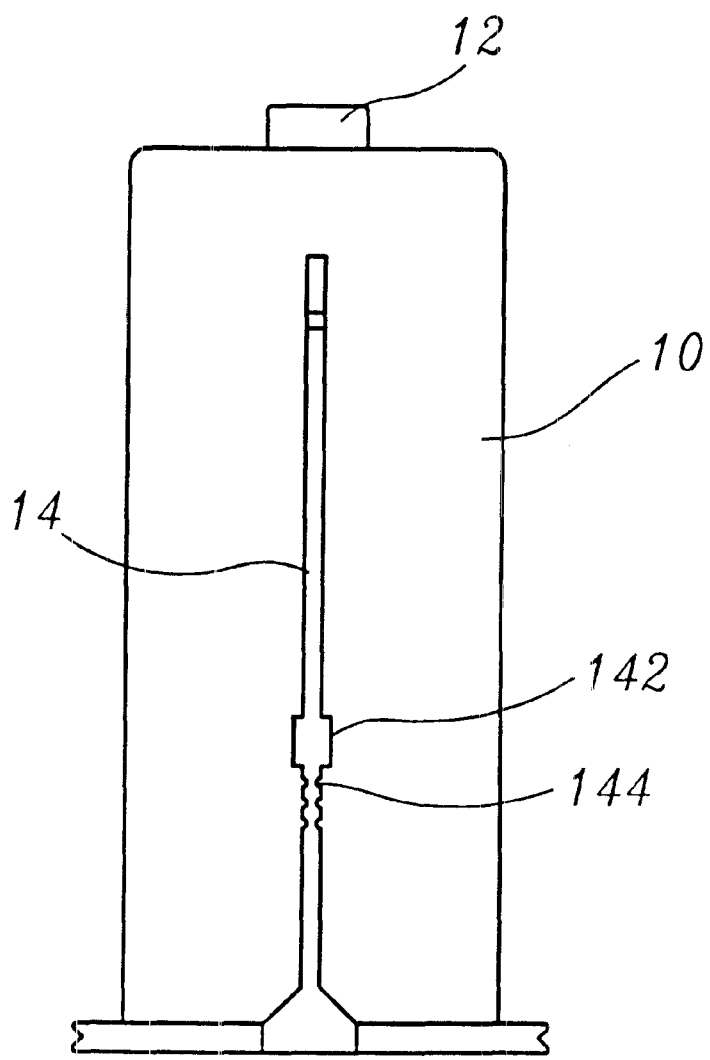
FIG. 3 is a side view of a preferred embodiment of the present invention, showing a guide groove.
Figure 5:
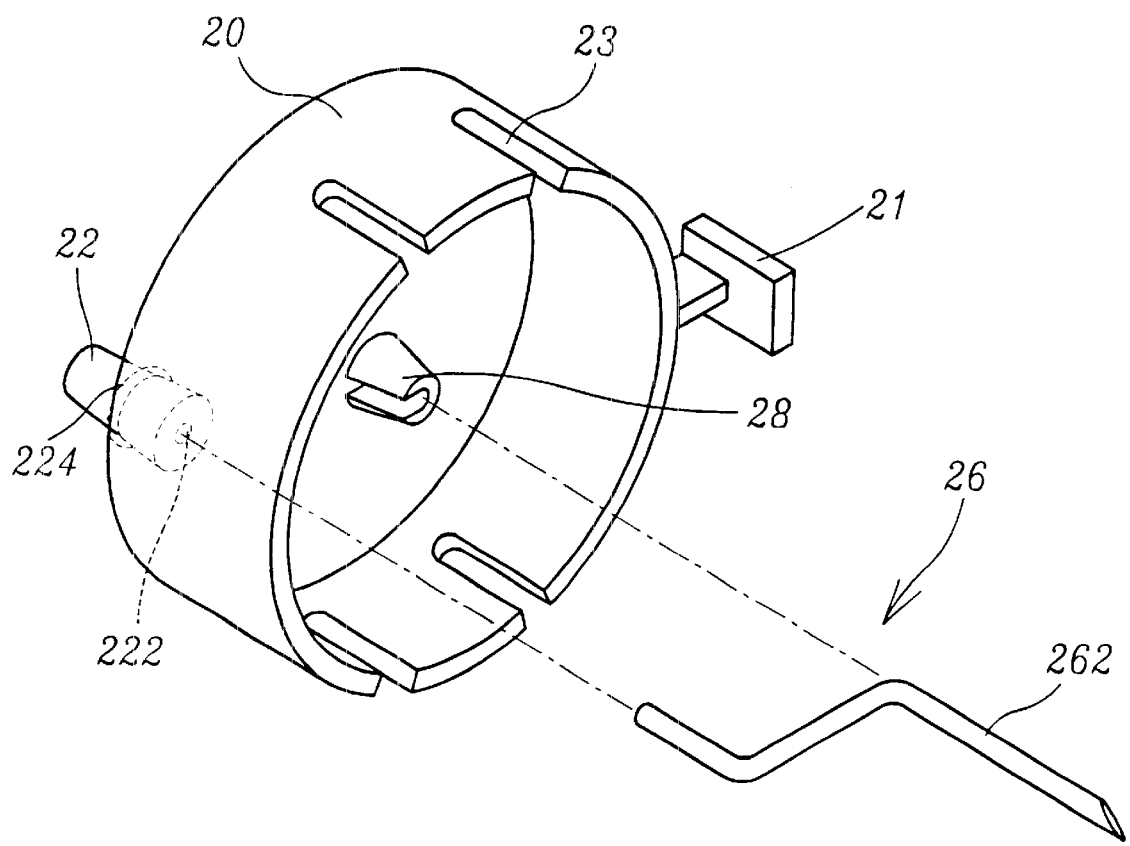
FIG. 5 is an explosive view of a reduced lining tube.

As FIGS. 1, 2 and 3 show, the present invention comprises a hollow barrel, a reduced inlet 12 eccentrically disposed at the top end of the barrel 10 and a guide slit 14 at the flank side of the barrel 10. The barrel comprises a reduced lining tube 20, an eccentric reduced portion 22 disposed at a position away from the center of the top end of the reduced lining tube 20, and an opening 24 disposed at the bottom thereof. The eccentric reduced portion 22 can be embedded into the reduced inlet 12, so as to project out of the reduced inlet 12. A needle head 30 can be wedged into the eccentric reduced portion 22, and a through guiding hole 222 is disposed at the center of the eccentric reduced portion 22 so that a needle 26 having a substantially Z-shaped portion can be fixed therein, and a lower needle tip 262 of the needle 26 can placed at the central axial line of the reduced lining tube 20. A fixing seat 28 is disposed at the center of the inner section of the reduced lining tube 20 for receiving and fixing the needle 26 therein. As FIG. 5 shows, a press plate 21 is further attached to the reduced lining tube 20 at the outer surface thereof and positioned in the guiding slit 14 to be utilized to drive the reduced lining tube to move in the longitudinal direction of the barrel 10.

A hook-shaped flange 16 is further disposed at a proper position of the inner surface of the barrel 10 so as to position the reduced lining tube 20 at the top end of the barrel 10 and not to slide loosely therein. Furthermore, at least one circular flange 224 is disposed around the eccentric reduced portion 22 and at least one circular groove 124 is disposed around the inner surface of the reduced inlet 12 to accommodate and position the circular groove 124. A plurality of small slits 23 are cut around lower side of the reduced lining tube 20, enabling the lower end of the reduced lining tube to keep proper elasticity. A vacuum tube 40 is further disposed inside the barrel 10, a elastic plug 42 is fixedly covered in an opening that is at the top end of the vacuum tube 40; the vacuum tube 40 is available in the market.

Figure 6:
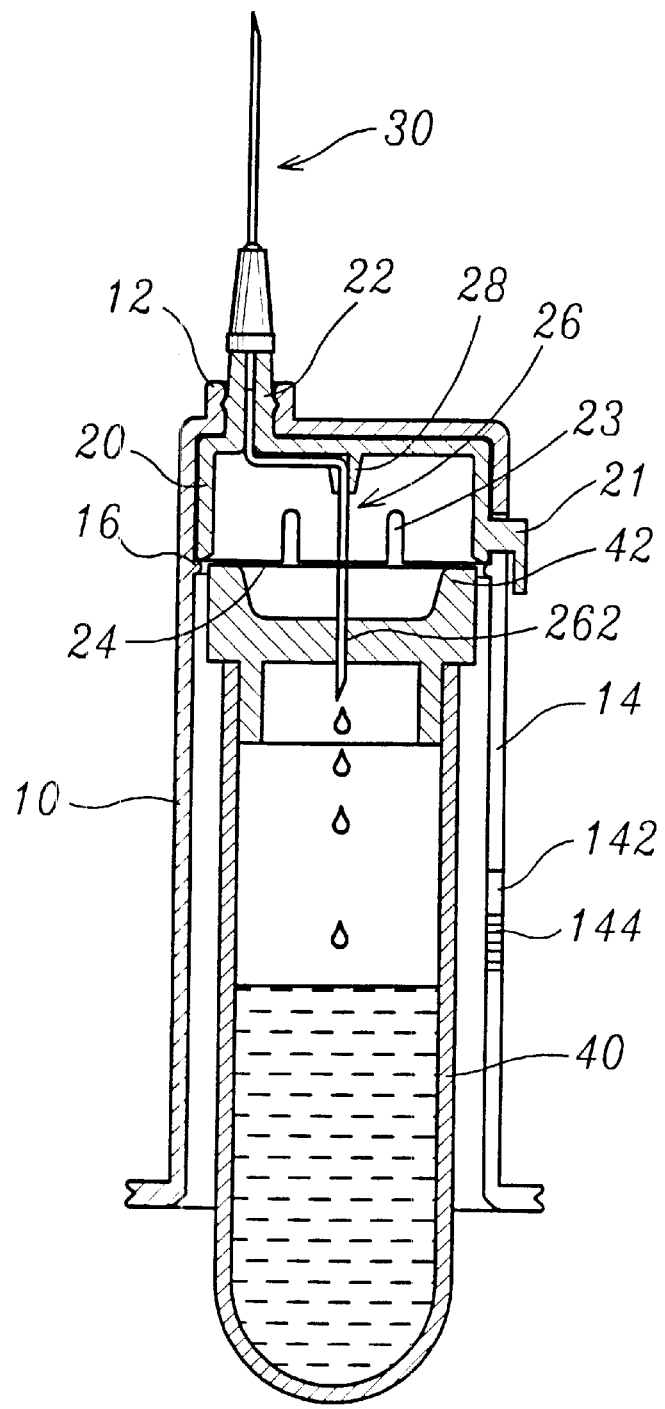
FIG. 6 is a longitudinal sectional view of a preferred embodiment of the present invention during use.

Please refer to FIG. 6, when the blood sampling is processing, strike the needle head 30 into the vein of a patient, then move the vacuum tube 40 toward the needle 26 inside the barrel 10 in order to make the lower needle tip 262 to prick through the plug 42 on the top of the cup 40, the blood from the vein of the patient will pass through the needle head 30, the guiding hole 222, then to the needle 26, and is finally led into the vacuum blood collecting cup 40. For the reason that the needle head 30, the eccentric reduced portion 22 and reduced inlet 12 are all eccentrically disposed and close to the circumference of the barrel 10, health care worker can prick the needle head 30 into the vein with a smaller inclined angle to the skin of the patient; it not only conforms to ergonomics, but prevent from the needle head piercing through the blood vessels.

Figure 4:
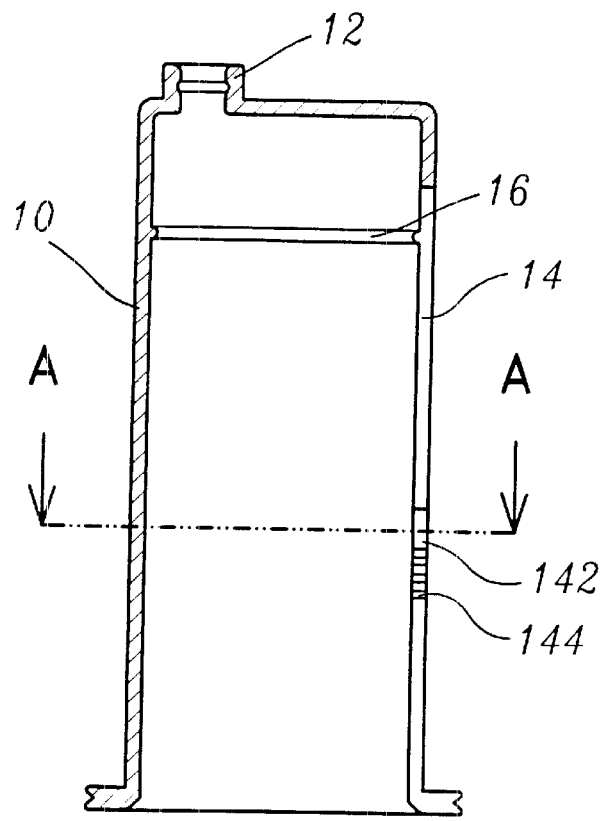
FIG. 4 is a longitudinal sectional view of a preferred embodiment of the present invention, showing the structure inside.
Figure 4A:
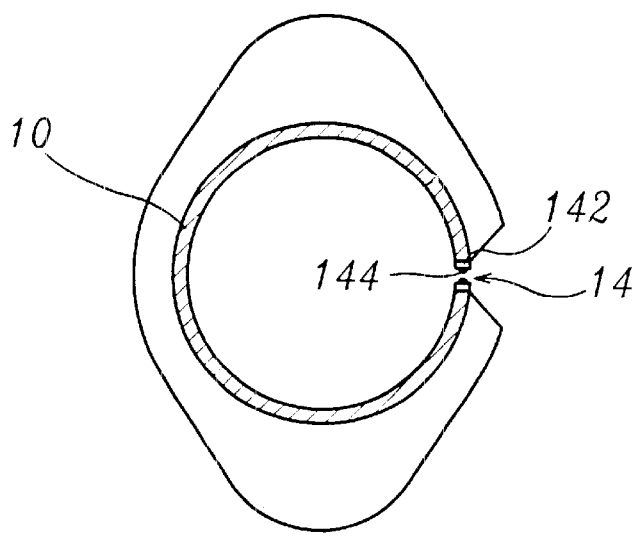
FIG. 4A is a sectional view of a preferred embodiment of the present invention when viewed from A—A direction of FIG. 4.
Figure 7:
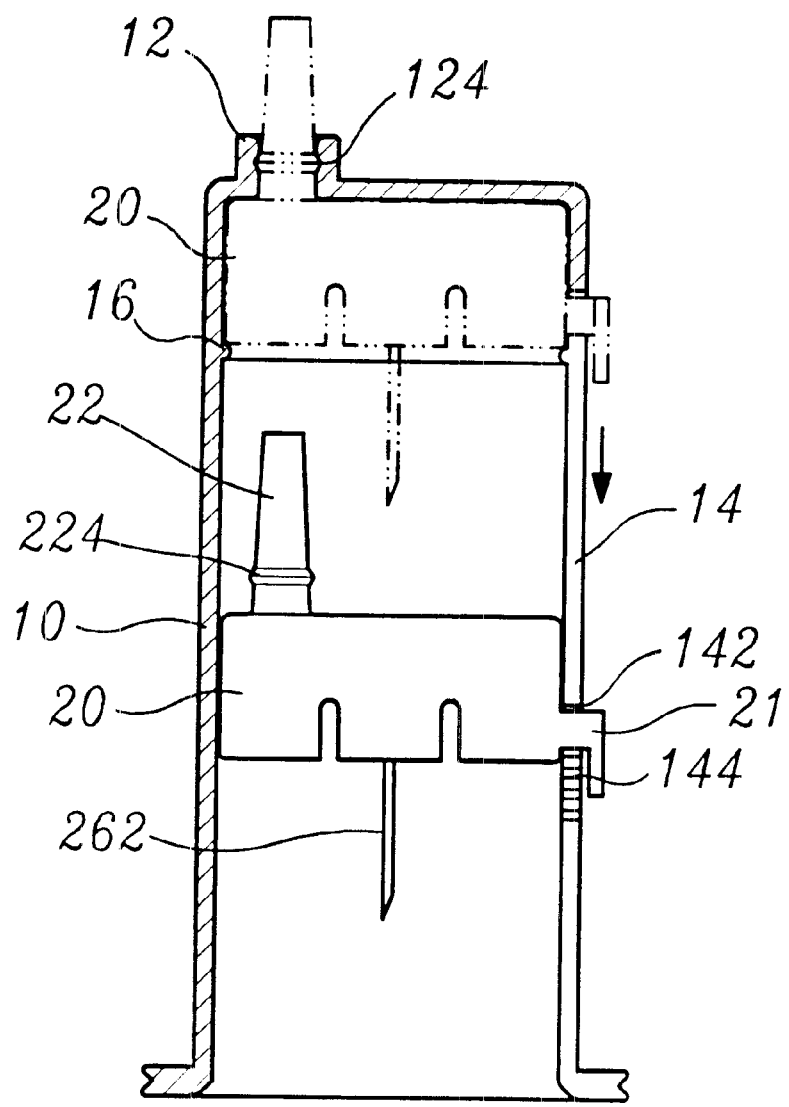
FIG. 7 is a longitudinal sectional view of a preferred embodiment of the present invention, showing a condition withdrawing a reduced lining tube back.

Now, refer to FIG. 7, after the blood sampling is over, press the press plate 21 backward to move the reduced lining tube back to prevent the needle head from pricking the health care workers. A stopping groove 142 is disposed at a proper position of the guiding slit 14, the width of the stopping groove 142 is larger than the width of the guiding slit 14 in order to stop the press plate 21 to move forward or backward when the press plate 21 is moved up to the stopping groove 142 to avoid the lower needle tip 262 at the lower end of the needle 26 to project out of the barrel 10 to cause danger. A plurality of bulging points 144 are disposed at the section of the guiding slit 14 below the stopping groove 142 to prevent the press plate 21 from slipping backward to drop out of the stopping groove 142 with the result that the lower needle tip is exposed out of the barrel 10, as shown in FIGS. 4 and 4A.

Figure 8:
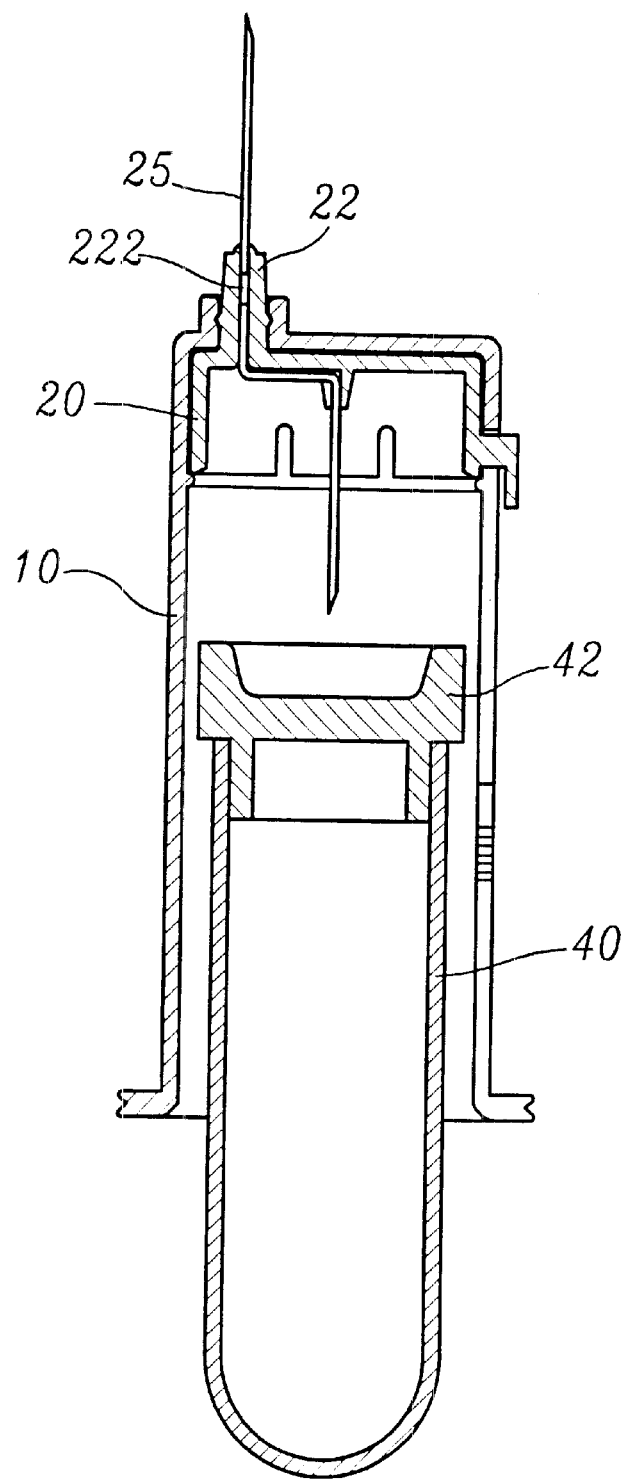
FIG. 8 is a longitudinal sectional view of a preferred embodiment of the present invention, showing a needle head being directly inserted into an eccentric reduced portion.
Figure 9:
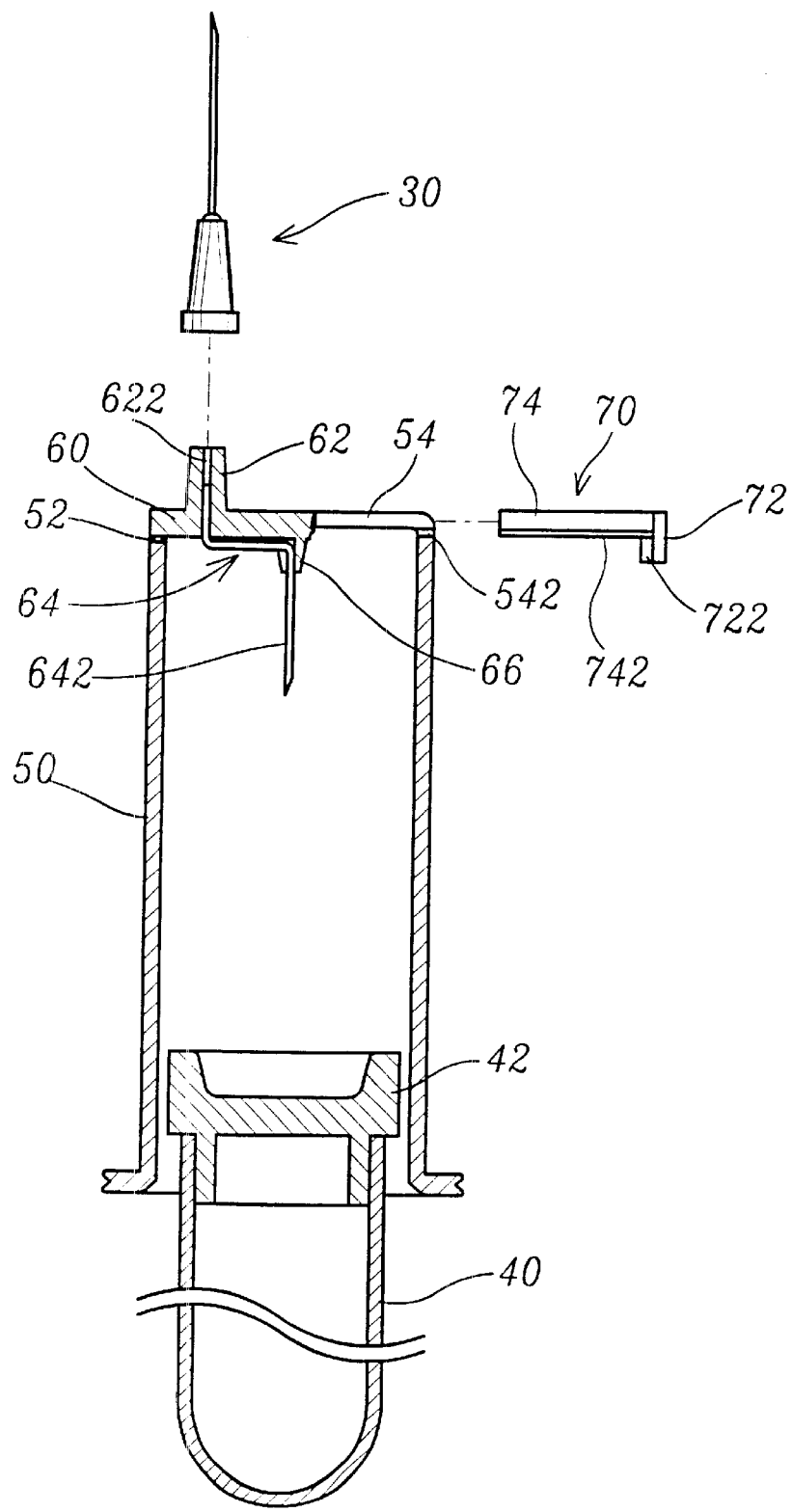
FIG. 9 is a longitudinal sectional view of another preferred embodiment of the present invention, showing a press plate being separated from a syringe.
Figure 10:
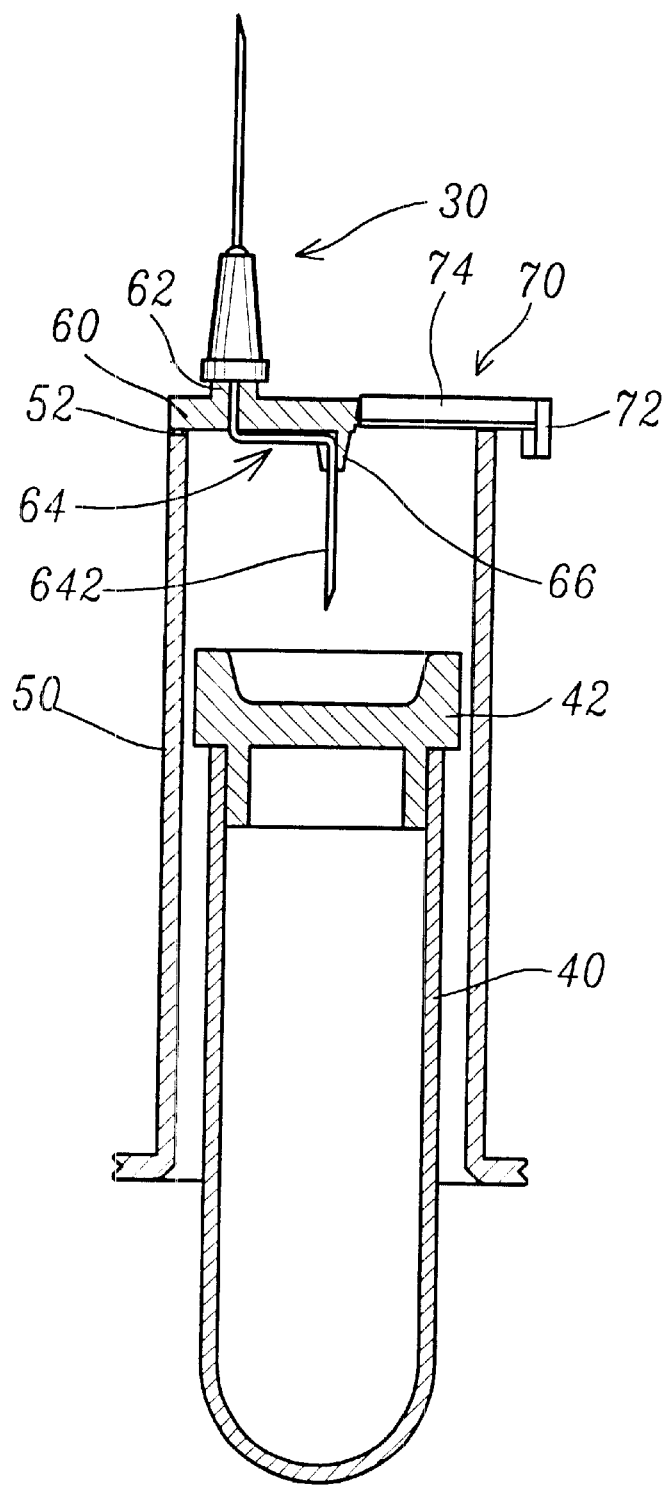
FIG. 10 is a longitudinal sectional view of another preferred embodiment of the present invention, showing a press plate being wedged into a syringe.
Figure 11:
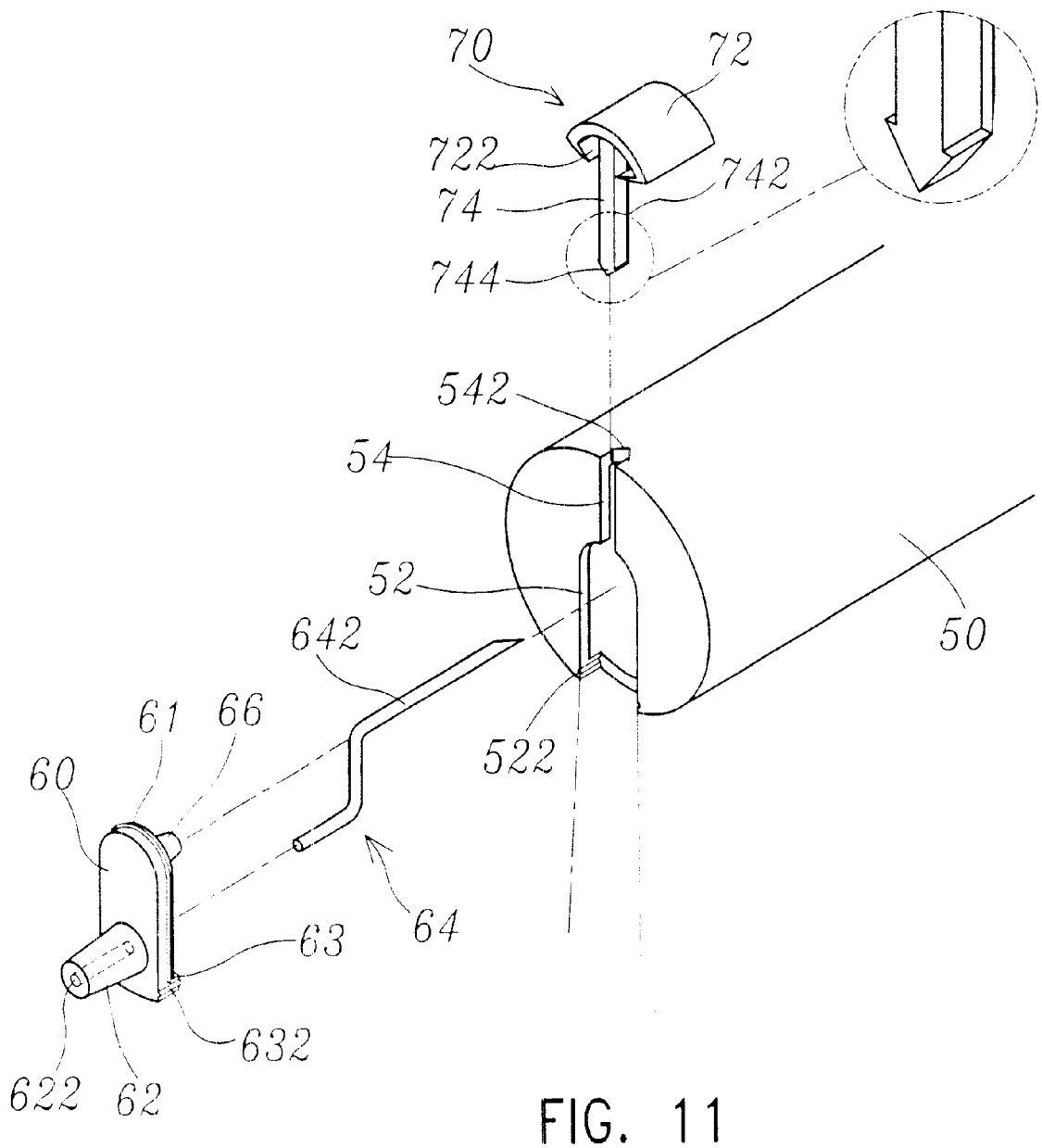
FIG. 11 is an explosive view of the front part of another preferred embodiment of the present invention.
Figure 12:
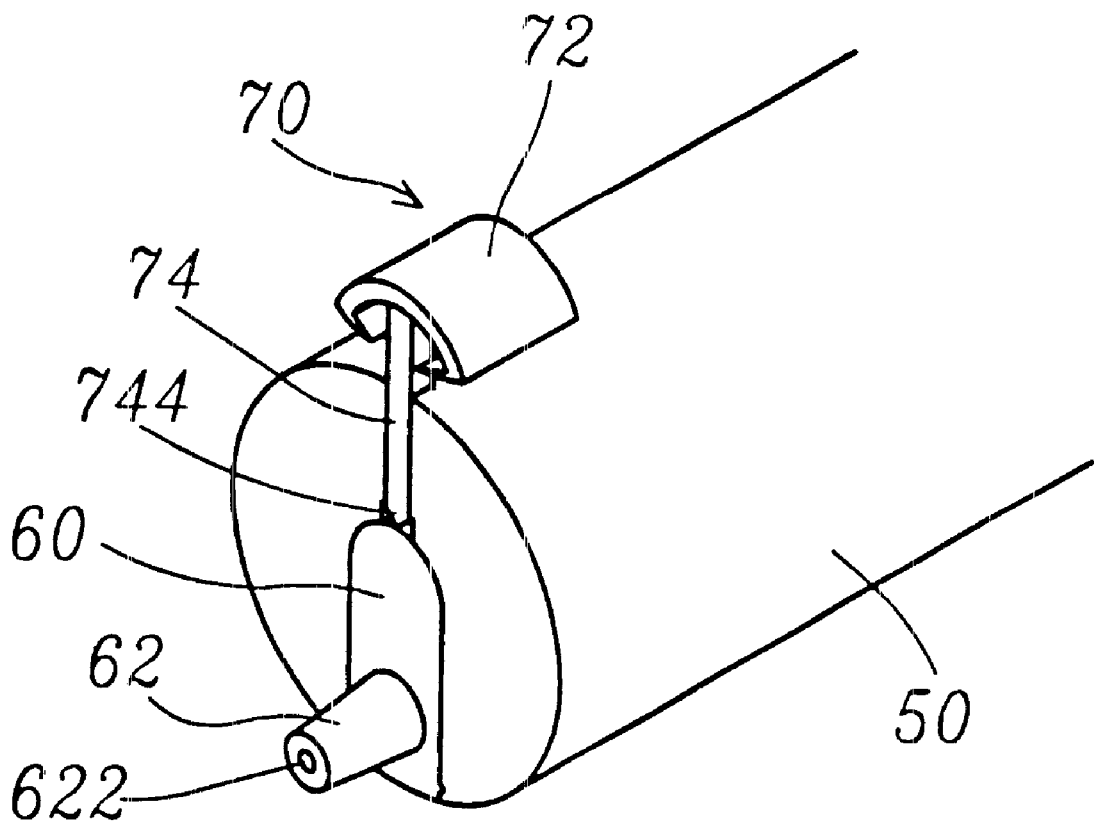
FIG. 12 is a perspective view of the front part of another preferred embodiment of the present invention.

Referring also to FIG. 8, a cannula needle can be located in the guiding hole 222 in advance when the eccentric reduced portion 22 of the reduced lining tube 20 is in production, so it doesn't need to insert the needle separately therein to save time and production cost.

FIGS. 9, 10, 11 and 12 show another preferred embodiment of the present invention. As the figures show, it comprises a hollow barrel 50, a directional sliding trench 52 transversely disposed at one side of the front end of the barrel 50, and a sliding slit 54 transversely disposed at another side opposite to the trench. A needle seat 60 and a press plate 70 are further disposed in the trench 52 and the slit 54 respectively. An eccentric reduced portion 62 is still disposed on the upper surface of the needle seat, and a needle head 30 may be wedged on the eccentric reduced portion 62. A guiding hole is pierced through the eccentric reduced portion 62 so that a needle 64 having a substantially Z-shaped portion can be fixed therein, and a lower needle tip 642 of the needle 64 can be placed at the central axial line of the reduced lining tube 50 firmly. A fixing seat 66 is disposed at the lower side of the needle seat 20 for receiving and fixing the needle 64 therein. For the reason that the needle seat 60 can be fixed firmly in the trench 52, a positioning flange 61 is disposed around the outside profile of the needle seat 60, and a small flange 632 is attached to each flank side of a convex plate 63. A guiding groove 522 is disposed at each flank side of the trench corresponding to the position of the flange 632 so as to fix the flange therein to prevent the needle seat from dropping out of the trench. Moreover, in order to assemble the needle seat 60 easily into the trench 52. The trench 52 has a certain degree of angle between its two sides so that the width of the opening at a first end is larger than at the opposing end, enabling the needle 60 to easily slip into the trench 52. The press plate 70 has an end face 72 and a guiding stick 74, the guiding stick 74 having a triangle shape strip 742 at its flank side, the sliding slit 54 having a triangle shape slit opening 542 at its flank side corresponding to the position of the strip 742, so as to move the press plate 70 as a guide. A triangle shape inverted hook is formed at the end 744 of the guiding stick 74 in order to be connected with the joint of the slit 54 and the trench 52 when the press plate 70 is positioned in the slit 54, enabling the press plate 70 not to slide backward to separate from the slit 54. An arc spring plate 722 is connected to the end of each flank side below the end face 72 to provide proper elastic force. A vacuum tube 40 is further disposed in the barrel 50, and an elastic plug 42 is firmly covered in the opening at the upper end of the vacuum tube 40, wherein the vacuum tube is available in the market.

Figure 13:
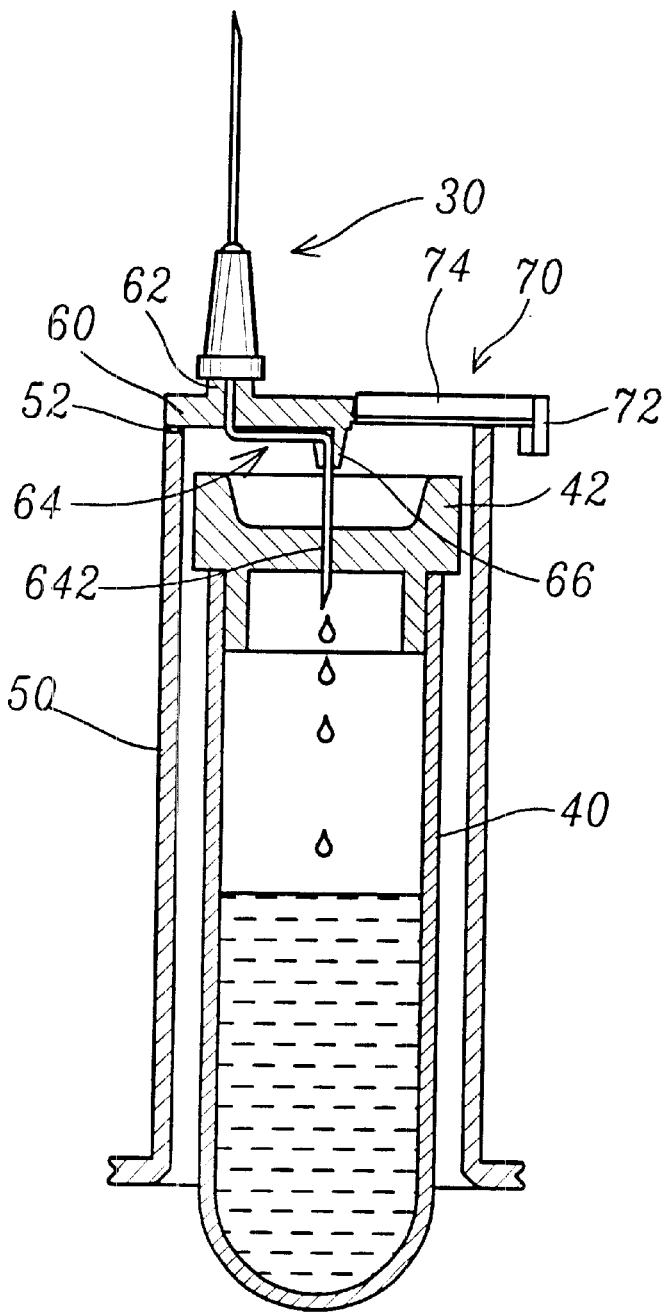
FIG. 13 is a longitudinal sectional view of another preferred embodiment of the present invention during use.
Figure 14:
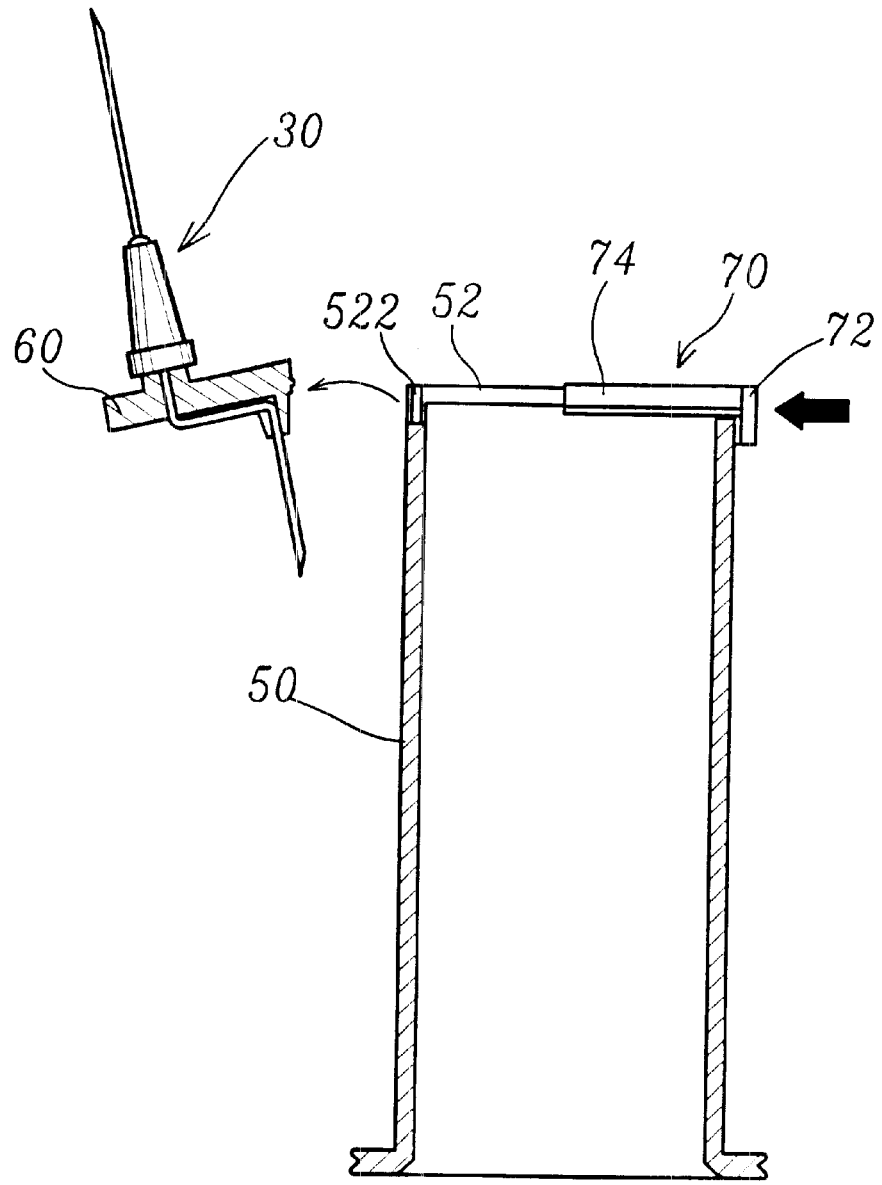
FIG. 14 is a schematic longitudinal sectional view of another preferred embodiment of the present invention, showing a needle seat being separated from a syringe.
Figure 15:
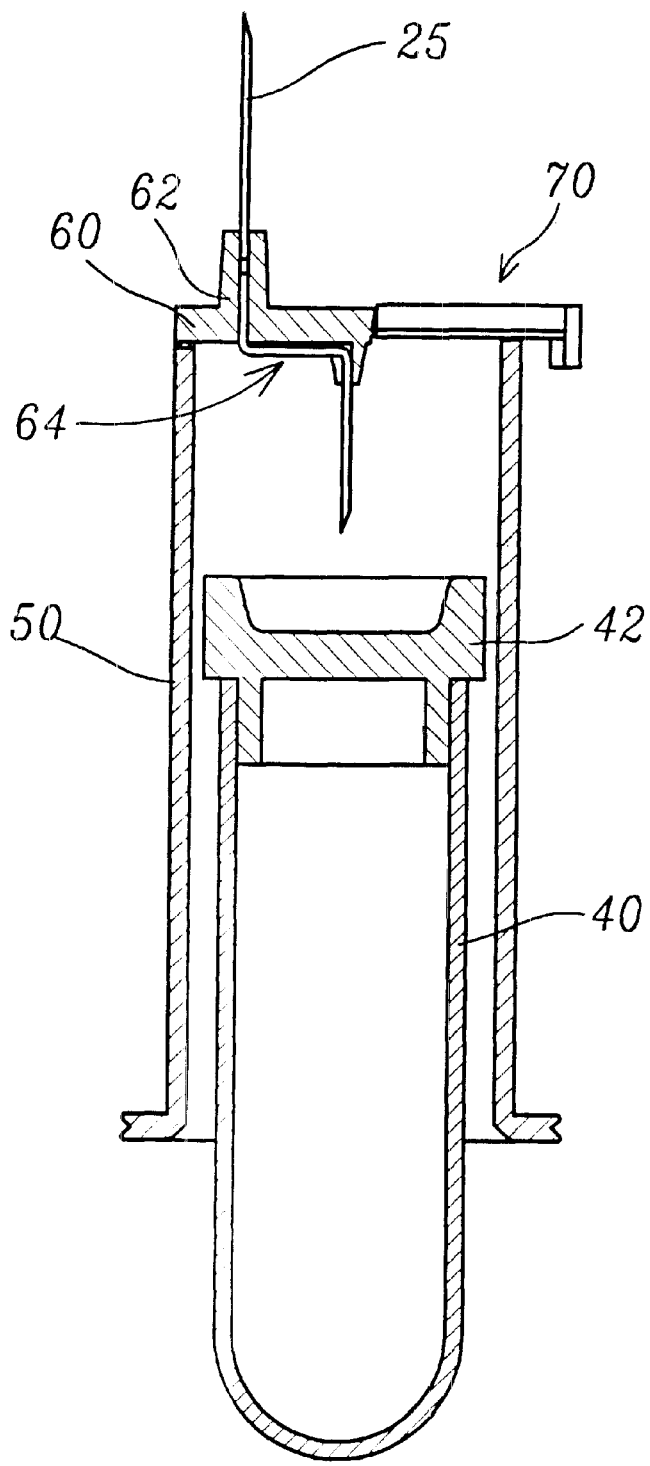
FIG. 15 is a schematic longitudinal sectional view of another preferred embodiment of the present invention, showing a needle seat being wedged into a syringe.

Next, referring to FIG. 13, when a blood is sampling, strike the needle head into the vein of a patient, then move the vacuum tube 40 toward the needle 64 inside the barrel 10 to let the plug 42 of the cup 40 to be pierced through, and the blood from the vein of the patient will pass through the needle head 30, the guiding hole 622, then to the needle 64, and is led into the vacuum blood collecting cup 40. When the blood sampling is over, may push the press plate 70 to separate the needle seat 60 simply from the trench and then to throw it in a needle head collector. Therefore, change a new needle seat 60 and needle head at the next blood sampling to avoid the infection of virus.

An advantage of the invention is that a proper thickness needle head 30 may be chosen to wedge on the eccentric reduced portion 22, 62. The needle head can be a conventional needle head instead of one having a particular design that requires a new mold to produce, such that it yields significant savings in costs. Moreover, for the purpose that a conventional vacuum blood collecting cup can be still used after the needle head 30 is eccentrically disposed, the needle 26, 64 of the invention is designed to have a substantially Z-shaped portion so as to position the lower needle tip 262, 642 of the needle 26, 64 at the center inside the barrel 10 and 50. Therefore, the lower needle tip 262, 642 can prick through the plug at the center, and as result, a particular structure of a vacuum blood collecting cup is unnecessary.

It is to be understood that the drawing is designed for purpose of illustration only, and is not intended for use as a definition of the limits and scope of the invention disclosed.

What is claimed is:

1. A safety vacuum syringe for blood sampling conformed to ergonomics comprising:

a hollow barrel, a directional sliding trench being disposed transversely at one side of a front end of said barrel, and a sliding slit being disposed transversely at another side opposite to said trench, a needle seat and a press plate being further disposed in said trench and said slit respectively, wherein an eccentric reduced portion is disposed on an upper surface of the needle seat, a guiding hole is disposed through the eccentric reduced portion to fix a needle having a substantially Z-shaped portion therein and a lower needle tip of the needle being placed at an central axial line of a reduced lining tube firmly, a needle head is further covered on said eccentric reduced portion, said press plate has an end face and a guiding stick, said guiding stick has a triangle shape strip at its flank side, said sliding slit has triangle shape slit opening at its flank side corresponding to a position of the strip, so as to move the press plate as a guide;

a vacuum tube, being disposed in said barrel, an elastic plug being covered on an opening at an upper side of said vacuum tube.

2. The syringe of claim 1, wherein a positioning flange is disposed around an outside profile of said needle seat, and a small flange is attached to each flank side of a convex plate, a guiding groove is disposed at each flank side of the trench corresponding to a position of said small flange so as to fix the flange therein to prevent the needle seat from dropping out of the trench.

3. The syringe of claim 1, a fixing seat is disposed at a lower side of said needle seat for receiving and fixing the needle therein.

4. The syringe of claim 1, wherein a triangle shape inverted hook is formed at an end of said guiding stick in order to connect with a joint of said slit and said trench when said press plate is positioned in said slit.

5. The syringe of claim 1, wherein an arc spring plate is connected to an end of each flank side below the end face of said press plate to provide proper elastic force.

6. The syringe of claim 1, wherein said trench includes first and second portions, the first portion having a greater width of opening than the second portion.

7. The syringe of claim 1, wherein a cannula needle is located in said guiding hole in advance to replace said needle head when said eccentric reduced portion of said reduced lining tube is in production.

8. An ergonomic safety vacuum syringe for sampling blood comprising:

a vacuum tube;

a hollow barrel having an end surface and a cylindrical side surface, said hollow barrel having a trench formed through said end surface, a needle seat positioned within trench, and a sliding slit formed through said end surface and said cylindrical side surface at another side opposite to said trench;

an eccentric reduced portion formed on an upper surface of the needle seat;

a first needle coupled to said eccentric reduced portion;

a second needle having a substantially Z-shaped portion extending between opposing first and second end portions, said first end portion being received within said eccentric reduced portion, said second end portion being positioned along a central axis of said hollow barrel; and, a press plate positioned within said sliding slit of said hollow barrel, said press plate having a guiding stick formed thereon said guiding stick having a triangular shaped strip at its flank side.

9. The ergonomic safety vacuum syringe for sampling blood as recited in claim 8, wherein a positioning flange is disposed peripherally about said needle seat, and a small flange is attached to each flank side of a convex plate, a guiding groove being disposed at each flank side of the trench corresponding to a position of said small flange so as to fix the flange therein to prevent the needle seat from dropping out of the trench.

10. The ergonomic safety vacuum syringe for sampling blood as recited in claim 8, wherein a fixing seat is disposed at a lower side of said needle seat for receiving and fixing the needle therein.

11. The ergonomic safety vacuum syringe for sampling blood as recited in claim 8, wherein a triangle shape inverted hook is formed at the end of said guiding stick in order to connect with a joint of said slit and said trench when said press plate is positioned in said slit.

12. The ergonomic safety vacuum syringe for sampling blood as recited in claim 8, wherein an arc spring plate is connected to an end of each flank side below an end face of said press plate to provide proper elastic force.

13. The ergonomic safety vacuum syringe for sampling blood as recited in claim 8, wherein said trench includes first and second portions, the first portion having a greater width of opening than the second portion.

14. The ergonomic safety vacuum syringe for sampling blood as recited in claim 8, wherein said first needle is a cannula needle is located in said guiding hole in advance when said eccentric reduced portion of said needle seat is in production.

* * * * *